United States Patent [19]

Verheijden et al.

[11] Patent Number: 5,760,315
[45] Date of Patent: Jun. 2, 1998

[54] SAMPLE COLLECTION DEVICE WITH ASSAY REAGENT AND BARRIER

[75] Inventors: Petrus Franciscus Hendrikus Maria Verheijden, Eersel; Adam Pieter Sylvana Visser, Veldhoven, both of Netherlands

[73] Assignee: Akzo Nobel N.V., Arnhem, Netherlands

[21] Appl. No.: 561,763

[22] Filed: Nov. 22, 1995

[30] Foreign Application Priority Data

Nov. 28, 1994 [EP] European Pat. Off. .............. 94203451

[51] Int. Cl.⁶ .............................. G01N 1/12; G01N 1/100
[52] U.S. Cl. ................................ 73/864.72; 73/863
[58] Field of Search ................... 73/863, 864, 864.71, 73/864.72, 864.73, 864.81, 864.11, 864.02, 61.41

[56] References Cited

U.S. PATENT DOCUMENTS

| | | | |
|---|---|---|---|
| 4,308,028 | 12/1981 | Elkins | 73/864.72 |
| 4,624,929 | 11/1986 | Ullman | 73/864.72 |
| 5,132,232 | 7/1992 | Parker | 73/864.02 |
| 5,460,781 | 10/1995 | Hori et al. | 73/863 |

FOREIGN PATENT DOCUMENTS

| | | |
|---|---|---|
| 9001870 | 5/1990 | Germany . |
| WOA 8804431 | 6/1988 | WIPO . |
| WOA 9311434 | 6/1993 | WIPO . |
| WOA 9422011 | 9/1994 | WIPO . |

*Primary Examiner*—Richard Chilcot
*Assistant Examiner*—Max H. Noori
*Attorney, Agent, or Firm*—Gregory R. Muir

[57] ABSTRACT

A sample collection device is described which comprises an absorbing material which can readily absorb and release test liquid, and which additionally comprises at least one assay reagent. The assay reagent is present in only part of the absorbing material, the remaining part of the absorbing material is located upstream the part comprising the assay reagent and serves as a reservoir for test liquid to be used as a washing fluid. The part of the absorbing material comprising the assay reagent is provided with means to prevent washing out of the assay reagent during sample taking, while allowing the availability of said assay reagent for test performance during or after sample taking.

23 Claims, 4 Drawing Sheets

SAMPLE COLLECTION DEVICE WITH ASSAY REAGENT AND BARRIER

The invention relates to a sample collection device comprising an absorbing material which absorbs a test liquid rapidly and is capable of an easy direct or indirect release of test liquid and additionally comprising at least one assay reagent. The sample collection device of the invention is specifically intended for home use or use by non-professional organisations, whereby sample taking is usually carried out by laymen or non skilled people.

In the state of the art there are various ways of collecting samples of body fluids such as urine, for the detection of specifically reacting substances. Methods for the detection of these substances can vary from chemical assays to immuno- and hybridisation assays. In conventional immunoassays and hybridisation assays, wherein precise quantitative results are required, test samples are usually taken by pipetting. In chemical assays or immunoassays which are for example carried out on test strips, usually paper strips, the test samples are taken by dipping the test strip (containing all reagents needed) into the test fluid or, for example, holding such a strip in a urine stream. However, as such a strip will contain reagents required for carrying out an assay for the detection of such a specifically reacting substance, there is a considerable risk of direct contact between the urine and the reagents, whereby the reagents may be washed out of the strip before the actual assay can take place.

In order to minimize the risk of washing out of the reagents, especially when the test is carried out by laymen, the test strips are usually surrounded by a housing or casing as described in European patents EP 291 194 and EP 383 619.

Another method for an easy and reliable collection of test samples, thereby avoiding direct contact with the assay reagents, is the use of a separate sample collection device such as the swab described in European patent EP 293 447. This swab comprises a tip of absorbent material, which is inserted—after sample collection—into a cylindrical tube comprising one or more sealed vessels or chambers with assay reagents in sequential order. The seal will break away or collapse when pressure of the collection device (swab) is exerted on the seal by physically pushing the collection device into and through each vessel. The collection device holder has appropriate stop points to allow for the collection device tip to enter the appropriate vessel and mix with its contents. A key feature of the vessels is that the tip and shaft of the collection device can pass through each of the vessels into a lower portion of the cylindrical tube and attached lower portion comprising a ligand receptor area. This ligand receptor area comprises a capture membrane which may be coated with a specific binding reagent to capture the reactants. Detection can take place visually or otherwise. Although the swab described in this patent application is suited for an easy collection of various types of test samples, including urine, the actual test performance seems to be complicated as a separate tube with sealed reagent chambers is needed next to a capture membrane area. In addition special requirements (appropriate stop points in the collection device holder) are needed to allow an adequate contact between the test sample and the reagents in the sealed chambers.

In patent application WO 86/03839 a solid phase diffusion assay is disclosed, wherein a porous body (swab) is described which contains a lyophilized labelled specific binding reagent, such as for example lyophilized gold sol labelled hCG antibodies. After wetting of this swab with test liquid (e.g. urine), the labelled specific binding reagent is dissolved or, when a particulate label is used, resuspended in the test liquid. The swab is subsequently brought into contact with an insoluble support, such as nitrocellulose paper, containing an immobilized specific binding reagent (e.g. hCG antibodies), whereby the test liquid, containing the dissolved or resuspended labelled specific binding reagent and possibly the analyte to be measured (e.g. hCG), diffuses from the swab into the insoluble support. When analyte is present in the test liquid this analyte and the labelled specific binding reagent will be bound by the immobilized specific binding reagent. The presence of analyte can be detected visually, for example as a red spot when gold sol particles are used as a label. The test performance is very easy and requires a minimum number of steps. However, with this type of test a background colour may be observed on the insoluble support if no provisions are made to remove excess of labelled specific binding reagent. Upon sample taking the swab used in this test comprises a solution or suspension of the labelled specific binding reagent, which is divided all over the swab and which is transported to the insoluble support as long as the swab is in contact with this support. Such a background colouration may impair the test results. Moreover, with this type of swab there is an important risk that the labelled specific binding reagent will be washed out of the swab during sample taking.

The present invention is concerned with the improvement of the known techniques, such as that referred to in the above application (WO 86/03839), especially with regard to reliability and robustness. These improvements have been achieved with a sample collection device comprising an absorbing material which is capable of absorbing a test liquid rapidly and is capable of an easy release of test liquid, and additionally comprising at least one assay reagent, characterized in that said assay reagent is present in the downstream part of said absorbing material, said part containing means to prevent that said assay reagent is washed out of the device during sample taking, said means being provided such that during or after sample taking said assay reagent is available for test performance, while the remaining part of said absorbing material is entirely or partly located upstream of said part comprising the assay reagent.

The assay reagent is included in only a part of the absorbing material of the sample collection device, which part is either located in the middle or bottom (downstream) section of said absorbing material. Upon sample collection, which is performed by dipping the absorbing material entirely in the test fluid or by holding the absorbing material in a urine stream, the assay reagent dissolves or—if the assay reagent is provided with a particulate label—resuspends in the test liquid. After sample collection the bottom (downstream) section of the absorbing material of the sample collection device is brought into contact with a test strip, membrane or the like (comprising for example an immobilized specific binding reagent) the assay reagent and the specifically reacting substance to be determined, if present, are transported from the sample collection device to the test strip where they will be bound by the immobilized specific binding reagent. The upper (upstream) section of the absorbing part of the sample collection device does not contain any assay reagent and serves as a reservoir for the test liquid. This test liquid is now used as a washing fluid to remove excess labelled specific binding reagent not bound to the immobilized specific binding reagent.

In order to allow a proper sample collection, that part of the sample collection device which comprises the assay reagent is provided with means to prevent that said assay reagent is washed out of the device during sample collection. The risk of washing out the assay reagent is especially relevant when the samples are collected unprofessionally (e.g. by laymen) and by holding the sample collection device in a urine stream.

In one preferred embodiment said means provides a cover, casing or envelop of a water repellent or water impervious material, which surrounds at least that part of the absorbing material which comprises the assay reagent. This cover, casing or envelop is constructed in such a way that during or after sample taking said assay reagent is available (or can easily be made available) for test performance. The thickness of this cover, casing or envelop varies depending on the type and pore size of the material used. Advantageously this water repellent material is a hydrophobic woven or non-woven material, hydrophobic paper or paper-like material and preferably a hydrophobic porous sintered material. The pore size of this hydrophobic porous sintered material should be such that penetration of test fluid is prevented, which is in general the case with a pore size of at most 100 µm. Preferably this pore size is below 50 µm. The hydrophobic porous sintered polymer material is preferably polypropylene, polyethylene, ultra high molecular weight polyethylene, a hydrophobic polyester and most preferably ethylene vinylacetate. Such a hydrophobic porous sintered polymer material as for example ethylene vinylacetate can easily be made hydrophilic by addition of wetting agents such as Tween 20 or Triton X 100. Therefore this material can in a hydrophobic state be used to prevent washing out of the assay reagent, while in a hydrophilic state it can be used as the absorbent material for a test fluid such as urine. A further advantage of ethylene vinylacetate is that it is flexible and therefore especially suited in combination with different types of test devices such as dipstick tests comprising a porous test strip.

When the hydrophobic porous sintered material is available in different pore sizes it may be advantageous to combine said hydrophobic material with a pore size of at most 100 µm, with the same material, but in a hydrophilized form, having a pore size large enough to permit a rapid absorption of test fluid. Hence on one hand the pore size can be chosen that small that penetration of test liquid is inhibited, thus preventing washing out of assay reagents, while on the other hand the same material, but in a hydrophilized form and preferably with a larger pore size to permit a rapid absorption of test fluid, can be used as the absorbing material.

Water repellent materials can also be obtained by treatment of hydrophilic materials with for example sprays comprising a wax in an organic solvent. Hydrophilic polymer materials can also be made water repellent by dispersing a filler material—such as $SiO_2$, $TiO_2$, $Al_2O_3$, SnO, Cu, ferrite and glass fibres—covered with for example a fluorocarbon chemically absorbing membrane (FCAM), in the hydrophilic polymer material. The pores of said hydrophilic polymer material are thereby filled with said FCAM coated particles of filler material. Advantageously the water impervious material is a foil, a semipermeable membrane, glass, rubber or a hot melt. Such a foil can be made of a polymer material, either a synthetic polymer material such as polypropylene or polyethylene or a natural polymer material as for example cellophane. Suitable foils can also be made of a non-polymer material such as aluminum. These foils have usually a thickness between 0.1 and 10 mm, depending on the material used. The foil is provided with openings to permit uptake of urine. These openings are sufficiently remote from the place where the assay reagent is located to prevent washing out by the urine. Glass can be used as a water impervious material for example in the form of a capsule or tube which contains the assay reagent. After sample taking the assay reagent can simply be released by breaking the capsule or tube for example by pressing. Further suitable water impervious materials are materials which can be applied in liquid form onto or into the absorbing material and which are cured for example upon cooling, drying or a chemical reaction induced by for example irradiation with ultraviolet light. In this way a kind of film or layer is formed on or in the absorbing material. Advantageously such a material is a hot melt, which comprises polymer materials which are in a solid state at ambient temperature, but which become a liquid at temperatures of for example 100° C. Other suitable materials comprise an epoxyresin, lacquer or glue.

A water impervious material can also be formed by solidifying the pores at the surface of a water repellent material.

All said means are positioned in such a way that the assay reagent is protected from washing out during sample collection, but that at the same time transport of the assay reagent and test liquid through the absorbing material is feasible (or can be made feasible), thus allowing the availability of these reagents for test performance.

In another embodiment the assay reagent is prevented from washing out by the urine by using a reagent composition that enables a controlled release of the assay reagent (controlled release composition). The controlled release composition, including the assay reagent, is present in the lower (downstream) part of the absorbing material. Said controlled release composition, usually comprises a binder/controlled release agent, a diluent and possibly a disintegrant. Advantageously said binder/controlled release agents are viscosity increasing agents, which can affect the rate of controlled release depending on their concentration, fatty materials or mixtures thereof, which are conventional excipients to control the rate of release, and water insoluble polymers with a delaying effect on the rate of release. Suitable viscosity increasing agents are selected from sugars, polyethylene glycols, gelatins, amylopectin, starch, carboxymethylcellulose, hydroxypropylcellulose, hydroxypropylmethyl-cellulose, polyvinylpyrrolidone, gums like arabic and guar gum, cellulose based and starch based materials and the like including mixtures thereof Suitable fatty materials are selected from fat alcohols, fatty esters, waxes, fatty acids,—such as stearyl alcohol, Precirol, magnesium stearate, hydrogenated castor oil, hydrogenated arachis oil, waxes like the excipient Gelucire which is composed of partial glycerides and polyglycides fatty esters, stearic acid—, fixed oils of vegetable origin, such as arachis oil, castor oil, fractionated coconut oil (Mygliols), ethyl oleate, maize oil and the like.

Suitable water insoluble polymers with an delaying effect on the rate of release are selected from polymethacrylates (e.g. Eudragit) and ethylcelluloses.

A diluent is always necessary in the reagent composition. Suitable diluents are selected from water insoluble calcium phosphates (di- and tribasic), calcium sulphate dihydrate, calcium carbonate, starch, modified starches, microcrystalline cellulose, water soluble sucrose, dextrose, lactose, mannitol, xylitol, sorbitol and the like and mixtures thereof.

Depending on the desired rate of controlled release, a particular concentration of disintegrant can be used, but a disintegrant is not always necessary. Suitable disintegrants are selected from microcrystalline cellulose (Avicel PH 101 and 102), purified wood cellulose, alginic acid, starch, sodium starch glycolate, guar gum, polyvinylpyrrolidone, cross-linked polyvinyl- pyrrolidone, ion exchange resins and the like and mixtures thereof.

In a preferred embodiment of the controlled release composition the assay reagent is mixed with hydroxypropylcellulose, starch and lactose or sucrose, whereupon a granulate is prepared. This granulate is subsequently mixed with ethylene vinylacetate powder and sintered according to procedures described in EP 299 299, U.S. Pat. No. 5,073,344 and EP 963 375. During this sintering process the particles of ethylene vinylacetate are fused together under controlled thermal conditions, thereby entrapping the granulate comprising the assay reagent. The degree of controlled release can be adjusted by varying the ratio of the components of the above mentioned controlled release composition. A controlled release composition is preferably used in combination with a water repellent material.

The absorbing material of the sample collection device can readily absorb test liquid, but also easily release this test liquid for example under mechanical pressure or capillary transfer. It can thus be a sponge-like material such as, for example, cotton wool, woven and non-woven materials, fibers bonded by extrusion, paper and paper-like materials. Preferably porous sintered hydrophilic and hydrophilized materials are used, such as hydrophilized polyethylene vinylacetate as well as other hydrophilized polyesters, hydrophilized polypropylene, hydrophilized polyethylene and hydrophilized ultra high molecular weight polyethylene. The pore size of these porous sintered hydrophilic and hydrophilized materials in the upstream section of the sample collection device is preferably larger than that of the materials in the downstream part to allow a rapid uptake of test liquid and to prevent washing out of assay reagent during sample taking. The absorbing material can also be provided with a colour to facilitate analyte identification.

The assay reagent which is present in the absorbing material, is preferably a member of a specific binding pair such as an antigen or antibody or their fragments, a DNA or RNA fragment, avidin or biotin. Such a specific binding reagent is preferably provided with a label. Although in principle all kinds of labels can be used, a preferred label for use in the present sample collection device according to the invention is a so-called particulate label. Most preferably a direct particulate label is used, which gives a direct visible test result without the need for additional reagents or equipment. Said direct particulate label comprises small coloured particles, such as gold sol particles, latex particles, dyestuff particles, liposomes or microcapsules including a dye, carbon-and selenium sol particles etc. These particles are as such insoluble in water, but resuspendible in solution. All these particulate labels are well known in the literature (see Clin. Chem. 27, 1157, 1981, EP 007 654, EP 032 270, EP 291 194, EP 154 749, EP 321 008).

Gold sol and carbon sol particles are particularly advantageous. The gold sol particles advantageously have a diameter of about 5 to 100 nm in size, while the preferred size of the carbon sol particles is 20 to 500 nm.

The assay reagent can be introduced in the sample collection device in a variety of ways. Advantageously it can directly be applied to the absorbing material by for example dispensing. When a porous sintered hydrophilic synthetic polymer is used as the absorbing material the assay reagent is preferably introduced as a granulate, which is mixed with the porous hydrophilic synthetic polymer prior to the sintering process (see EP 299 299, U.S. Pat. No. 5,073,344 and EP 963 375). Such a granulate comprises a sugar, for example trehalose, next to the assay reagent. During this sintering process particles of polymer are fused together under controlled thermal conditions to produce a firm, but porous structure, whereby the granulate comprising the assay reagent is entrapped.

The assay reagent can also be applied in an indirect way, for example by introduction of a porous carrier impregnated with the assay reagent into an interior space in the absorbing material. Suitable porous carriers are for example paper discs, porous sintered materials or nonwoven materials. Preferably the assay reagent is introduced into said interior space in a freeze-dried form, for example as accuspheres. It is also possible to include the assay reagent in capsules or tubes, which are subsequently inserted into the absorbing material.

The sample collection device also comprises a handle, which is advantageously produced from a material which is water impervious, such as thermoplastic material, polystyrene or the like. This handle can for example be provided with a colour. This colour can serve for analyte identification and thus facilitate handling of larger numbers of different samples.

The present invention is further directed to a device and a method for the detection of a specifically reacting substance comprising the sample collection device described above.

Such a device advantageously contains a membrane, test strip or the like consisting of a material which transports the test liquid essentially by capillary forces. Preferably absorbent, porous or fibrous material is used, which is suitable for rapid uptake of liquid. The device also contains additional assay reagents required for the detection of said specifically reacting substance. These additional assay reagents are preferably an antigen or antibody or their fragments, a DNA or RNA fragment, avidin or biotin, protein A and the like. In its simplest form the device is a membrane, test strip or the like containing the additional assay reagents. Preferably said device is a filter test and most preferably a porous test strip test. Numerous examples have been described for these types of tests (see EP 180 638, EP 291 194, EP 349 215). Of particular relevance is the apparatus described in our pending patent application no. PCT/EP 94/00899. This apparatus comprises a housing equipped with an interior space and an opening for introduction of the sample collection device. On the housing a holding device is located which holds a test strip consisting of a material that transports the test liquid essentially by capillary forces and which comprises an immobilized binding reagent such as a member of a specific binding pair, preferably an antibody. Transfer of the liquid sample, containing the reagent mixture, from the sample collection device to the test strip can be achieved by contacting. This transfer can be facilitated by special means in the housing, such as an elevation on the inner wall, or by bending the top end of the test strip so that it extends into the interior space of the housing.

Exemplary embodiments of the invention are explained in detail hereinafter.

All these igures are drawn to a scale of 2:1.

Figure 1:
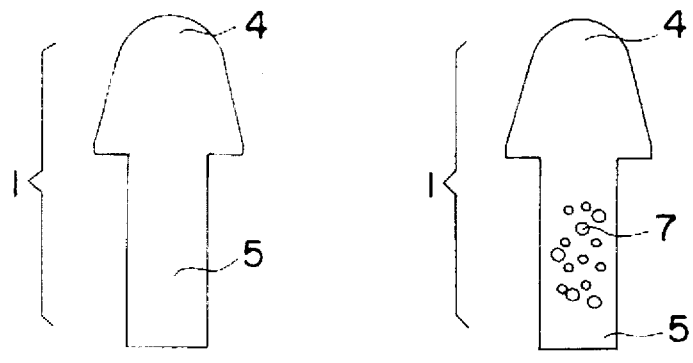
FIG. 1 shows an axial cross-section of a first embodiment of the sample collection device described in the present invention.

The sample collection device of FIG. 1 comprises two sections 1 and 3 comprising porous sintered ethylene vinylacetate hydrophilized with a wetting agent, and a section 2 containing untreated ethylene vinylacetate (being the water repellent material). The device further contains a handle 8. Section 1 has a top end 4 and an elongated part 5, which fits into the interior space 6 of section 2. The assay reagent (labelled specific binding reagent 7) is introduced into the interior space 6 in a freeze-dried form or impregnated into a porous carrier.

Figure 2:
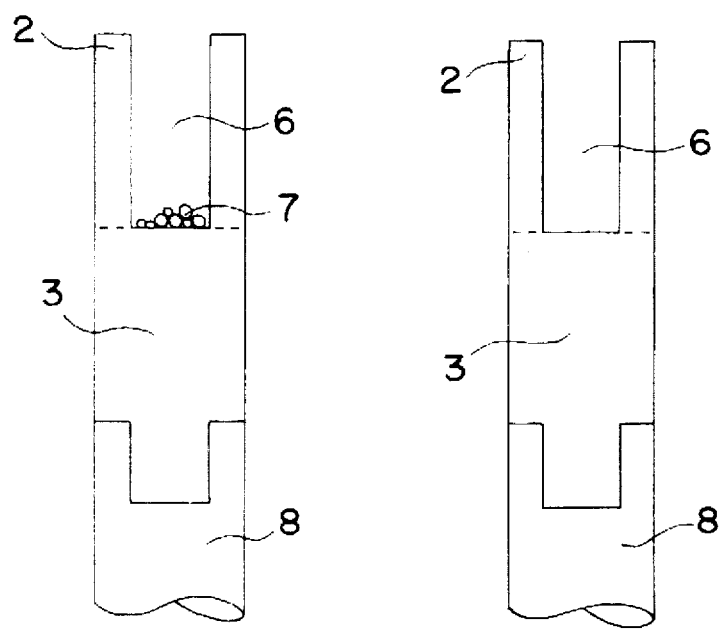
FIG. 2 shows an axial cross-section of a modification of the first embodiment of the invention.

The sample collection device of FIG. 2 is a modification of the one depicted in FIG. 1, whereby the elongated part 5 of section 1 is impregnated with the assay reagent (labelled specific binding reagent 7).

Figures 3, 4:
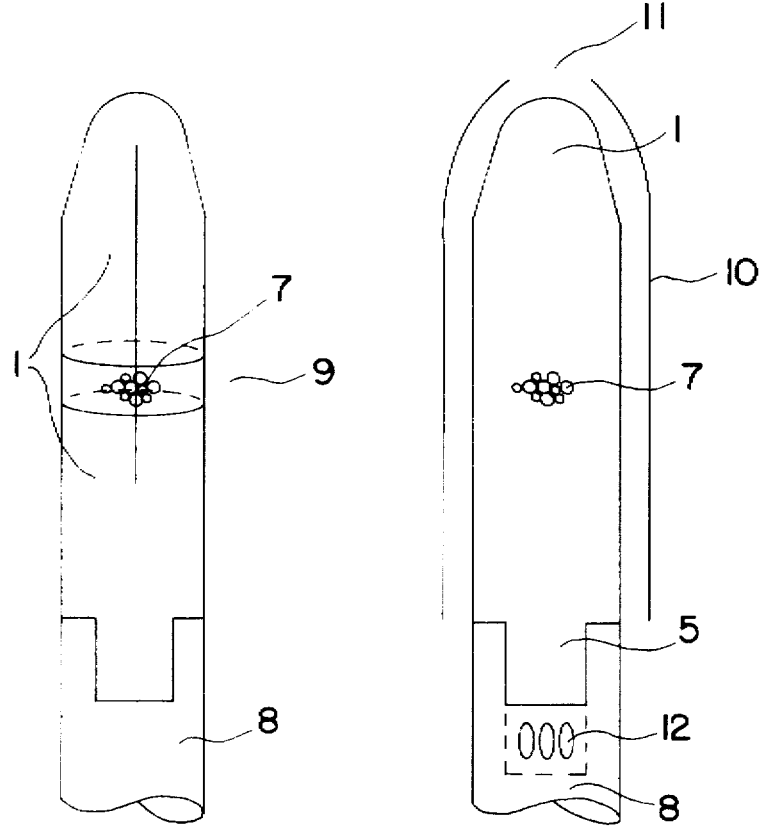
FIG. 3 shows an axial cross-section of a second embodiment of the invention.
FIG. 4 shows an axial cross-section of a third embodiment of the invention.

The sample collection device of FIG. 3 contains a section 1 with porous sintered hydrophilic or hydrophilized material. A zone in the middle of section 1 is impregnated with the labelled specific binding reagent 7. This reagent can also be entrapped in this zone. This zone is surrounded by a cylindrical element 9 comprising a water impervious material.

In the sample collection device of FIG. 4, the elongated part 5 of the hydrophilic section 1 extends into the handle 8, which contains openings 12 to permit uptake of urine when holding the device in the urine stream. Section 1 is surrounded by a water impervious foil 10 with an opening 11 to permit the outflow of the reagent mixture when brought into contact with a test membrane or test strip. The labelled specific binding reagent 7 is included in the middle part of section 1.

Figure 5:
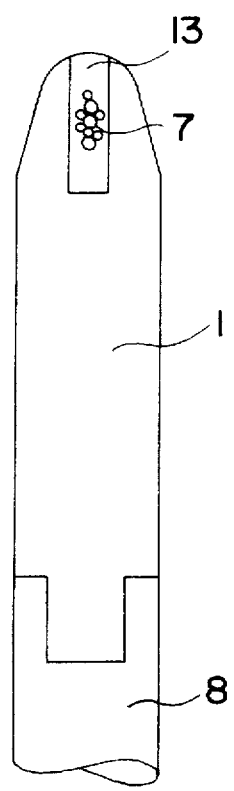
FIG. 5 shows an axial cross-section of a fourth embodiment of the invention.

In the sample collection device of FIG. 5 a glass capsule or tube 13, containing the labelled specific binding reagent 7, is inserted into the hydrophilic section 1. This capsule is broken after sample taking to make the assay reagent available for test performance.

Figure 6:
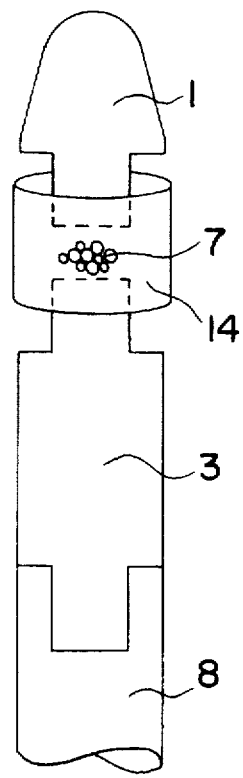
FIG. 6 shows an axial cross-section of a fifth embodiment of the invention.

The sample collection device of FIG. 6 contains two hydrophilic sections 1 and 3. The labelled specific binding reagent 7 is located between these two sections in a freeze-dried form or impregnated into a porous carrier. The two sections 1 and 3 are connected by a cylindrical element 14 comprising a water impervious material. This cylindrical element also surrounds the labelled specific binding reagent 7.

Figure 7:
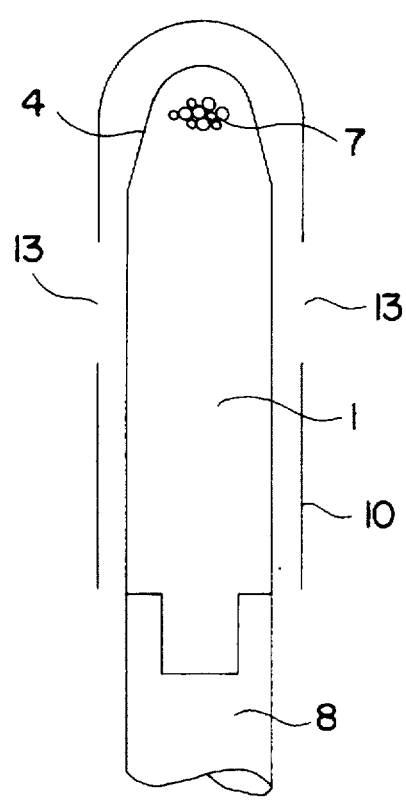
FIG. 7 shows an axial cross-section of a sixth embodiment of the invention.

In the sample collection device of FIG. 7 the hydrophilic section 1 is surrounded by a water impervious foil 10 with openings 13 to permit uptake of urine when holding the device in the urine stream. The labelled specific binding reagent 7 is included in the top end 4 of section 1. Prior to further test performance an additional opening should be made in the water impervious foil 10 at the top end 4, to allow contact between the reagents in the sample collection device and those of a test strip or test membrane.

Figure 8:
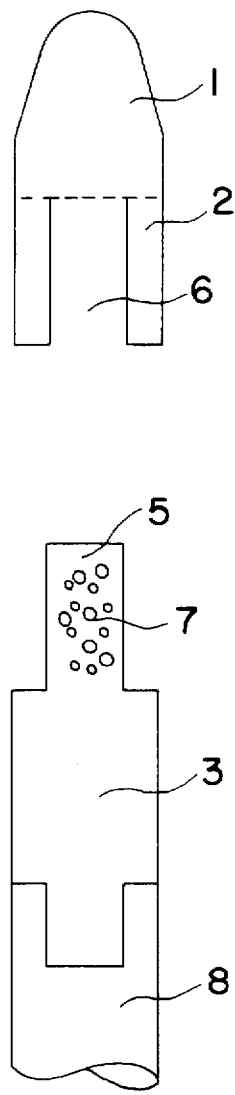
FIG. 8 shows an axial cross-section of a modification of the first embodiment of the invention.

The sample collection device of FIG. 8 is a modification of that depicted in FIG. 2, whereby section 2 comprises an interior space 6 and section 3 an elongated part 5, which fits in the interior space 6. The pore size of the porous sintered ethylene vinylacetate in the elongated part 5 is smaller than that in the remaining part of section 3. Both materials are hydrophilized with a wetting agent. Furthermore section 1 comprises porous sintered polyethylene hydrophilized with a wetting agent, whereby the pore size of this material is smaller than that of the material in the elongated part 5. The labelled specific binding reagent is either entrapped or impregnated in the elongated part 5 or located between the elongated part 5 and the inner wall of the interior space 6. Said reagent is protected from washing out by the hydrophobic ethylene vinylacetate in section 2.

The sample collection device according to the present invention can be used in a method for the detection of a specifically reacting substance such as an antigen, hapten, antibody or antibody fragment, DNA- or RNA fragment, and in particular hCG, in a test liquid such as urine.

Such a method comprises for example the following steps:

taking a sample of test liquid by means of said sample collection device, whereby the specifically reacting substance, if present in the test liquid, reacts with the assay reagent.

contacting the sample collection device with, for example, a porous test strip comprising an immobilized specific binding reagent, whereby the test liquid containing the reagent mixture will be transported from the sample collection device to the test strip, whereupon the complex formed between the specifically reacting substance and the assay reagent, will be bound by the immobilized specific binding reagent.

visual reading of the assay results.

By way of example only, some preferred embodiments of the invention will now be described in detail. The sample collection device used is that depictured in FIG. 8, while in addition a test strip (comprising an immobilized specific binding reagent and a control reagent), holding device and housing are used as described in our pending patent application no. PCT/EP 94/00899.

EXAMPLE 1

1. Preparation of gold sol labelled monoclonal hCG antibodies (labelled specific binding reagent)

Gold sols with an average particle diameter of 50 nm (A 540=5.0) are prepared by Frens (Nature Physical Science Vol. 240, 1973, 20). A solution of 1 mg monoclonal hCG antibodies (beta-unit specific and prepared essentially as described in EP 045 103) per ml sodium chloride (9 g/l) is adjusted to pH 8.0 using 0.1M sodium hydroxide.

1 l of the gold sol solution is adjusted to pH 8.0 with 0.1M sodium hydroxide, mixed with 20 ml of the monoclonal hCG antibody solution and subsequently postcoated by adding 40 ml of a 20M polyethylene glycol solution, pH 8.0. The postcoated gold sol labelled hCG antibodies are sedimented by centrifugation for 20 min. at 3500 g at ambient temperature. After removing the supernatant by suction, the gold sol pellet is resuspended to an A 540 value of 50.0 in a solution containing 2% (v/v) foetal calf serum, 160 g/l sucrose, 2% (w/v) Triton X100 and 1M Tris, pH 8.0.

2a. Preparation of hydrophilized ethylene vinylacetate 60 g ethylene vinylacetate powder (particle size 350 µm or 500 µm) is mixed with 100 ml ethanol containing 1% Tween/Span (1:3 w/v). This mixture is left to stand for 10 min. under gently shaking, decanted to remove excess ethanol and finally dried overnight at 20°-25° C.

2b. Preparation of hydrophilized polyethylene 60 g polyethylene powder (particle size 50 µm) is mixed with 100 ml ethanol containing 1% Tween/Span (1:3 w/v) and handled in the same way as described under 2a.

2c. Preparation of hydrophobized ethylene vinylacetate 60 g ethylene vinylacetate powder (particle size 350 μm) is mixed with 100 ml isopropylethanol containing 1% Fluorresin (w/v). This mixture is left to stand for 10 min. under gently shaking, decanted to remove excess isopropylethanol and finally dried overnight at 20°–25° C.

3. Preparation of the sample collection device

The sample collection device depictured in FIG. 8 is prepared in two parts A and B respectively. Part A comprises the hydrophilic section 1 and the hydrophobic section 2, while part B comprises the hydrophilic section 3 with the elongated part 5 comprising the gold sol labelled monoclonal hCG antibodies (labelled specific binding reagent 7).

Part A is prepared in a mould which is constructed of two mould parts: one mould part for the hydrophilic section 1 and another mould part for the hydrophobic section 2. The mould part for section 1 is filled with hydrophilized polyethylene powder (as described under 2b), while the mould part for section 2 is filled with hydrophobized ethylene vinylacetate powder (as described under 2c). Subsequently the materials are sintered according to procedures described in EP 299 299, U.S. Pat. No. 5,073,344 and EP 963 375 and jacked.

Part B is also prepared in a mould which is constructed of two mould parts: one mold part for the elongated part 5 of the hydrophilic section 3 and another mold part for the remaining part of section 3. The mold part for the elongated part 5 is filled with hydrophilized ethylene vinylacetate powder, particle size 350 μm (as described under 2a), while the mold part for the remaining part of section 3 is also filled with hydrophilized ethylene vinylacetate, but with a particle size of 500 μm (as also described under 2a). These materials are then subjected to a sintering process as mentioned above.

After sintering of parts A and B the pore sizes of the various sections are measured. Section 1 has a pore size of 20 μm, the pore size of section 2 is 100 μm, the elongated part 5 of section 3 has a pore size of 120 μm, while the pore size of the remaining part of section 3 is 180 μm.

Subsequently 4–8 μl of a suspension of gold sol labelled monoclonal hCG antibodies (see under 1) is dispensed onto the end of the elongated part 5 of section 3, using a peristaltic pump, and dried for 5 to 6 min. at 45° to 50° C. with a dry and warm airflow.

After drying of the gold sol labelled monoclonal hCG antibodies, part A and part B are joined and welded. Welding is performed by positioning a welding plate of particular design between part A and part B before assembling, and slightly pressing these parts against the hot plates. The ethylene vinylacetate material starts melting and after about 1 second the plates are removed. By slightly pressing the two parts against each other a tight joint is accomplished.

4. Preparation of a solution of polyclonal hCG antibodies

Polyclonal antibodies against hCG are prepared according to conventional techniques. 6 g of immunopurified hCG antibodies are dissolved in 1 l of a solution containing 3.5 mM Tris, pH 8.0, and 9 g/l sodium chloride.

5. Preparation of a solution of monoclonal rabbit anti-mouse antibodies

Monoclonal rabbit anti-mouse antibodies (anti-kappa) are prepared according to conventional techniques. 3 g of monoclonal rabbit anti-mouse antibodies are dissolved in 1 l of a solution containing 3.5 mM Tris, pH 8.0, and 9 g/l sodium chloride.

6. Preparation and assembly of test strips

On a rectangular sheet of glass paper (thickness 0.6 mm, basis weight 100 g per m$^2$) measuring 100 mm in length and 7 mm in width a detection zone, containing an immobilized specific binding reagent, is formed on each test strip by pipetting, 40 mm from the bottom edge, 1 μl of a solution of polyclonal hCG antibodies (see under 4). A second zone, meant as a control zone, is formed on each test strip by pipetting, 50 mm from the bottom edge, 1 μl of monoclonal rat anti-mouse IgG (see under 5).

Finally these test strips are assembled in an apparatus as described in our pending patent application no. PCT/EP 94/00899.

7. Assay procedure

The sample collection device (see under 3) is held in the urine stream, whereby the hydrophilic sections 1 and 3 rapidly absorb the urine. The urine also gets into contact with the dried gold sol labelled monoclonal hCG antibodies, which resuspend in the urine and which will bind to the hCG in the urine, if present. The sample collection device is subsequently brought into contact with the test strip in the apparatus as described under point 6. The urine, containing the hCG—gold sol labelled monoclonal hCG antibody complex, is released from the sample collection device upon contact with the test strip and transported through the test strip by capillary action. The hCG—gold sol labelled monoclonal hCG antibody complex is then fixed by the immobilized polyclonal hCG antibodies on the test strip, whereupon the presence of hCG can be detected by visual reading the colour. Furthermore the test performance can be controlled by observing the colour at the control zone.

The time between sample taking and bringing the sample collection device into contact with a test membrane or test strip can be varied. As a consequence the pre-incubation time between the specifically reacting substance and the assay reagent is varied as well. By increasing this preincubation time an increased assay sensitivity is obtained, which is a major advantage of the use of a separate sample collection device.

Alternatively, the assay time can be reduced, while maintaining the assay sensitivity, by decreasing the distance between the detection spot and the area where the sample collection device is brought into contact with the test strip. Another possibility to reduce the assay time, while maintaining the assay sensitivity and the distance between the detection spot and the contacting area (see above), is the use of a smaller volume of the assay reagent, possibly in combination with an adapted assay reagent composition such as a lower sugar concentration.

EXAMPLE 2

Preparation of reagents, test strips and assay procedure are identical to those described in Example 1. However, the gold sol labelled hCG antibodies are introduced into the absorbing material as a granulate, while the sample collection device is prepared in a different way:

1. Preparation of a granulate of gold sol labelled monoclonal hCG antibodies 1 g starch and 8.6 g sucrose are thoroughly mixed. To this mixture 10 ml of a suspension of gold sol labelled monoclonal hCG antibodies (see Example 1, point 1) are added. After mixing until a homogeneous mass is obtained, 1 ml of a solution of 0.3 g hydroxypropylcellulose in distilled water is added. After thorough mixing the mixture is dried during 48 hours at 40° C. under vacuum. The dried material is sieved (pore size sieve is 300 μm) and the achieved granulate stored in vials in an desiccator containing silicagel.

2. Preparation of sample collection device

Part A (see Example 1, point 3) is prepared in essentially the same way as described in Example 1.

Part B is also prepared in the same way as described in Example 1, except for the mould part for the elongated part 5 which is filled with a mixture of hydrophilized ethylene vinylacetate powder (particle size 350 μm) and the granulate of gold sol labelled monoclonal hCG antibodies (see under 1). Subsequently the materials are sintered according to procedures mentioned under point 3 of Example 1.

We claim:

1. A sample collection device comprising:

an absorbing material capable of absorbing a test liquid and capable of release of said test liquid, said absorbing material having an upstream part and a downstream part and at least one assay reagent; and a handle separate from said absorbing material for holding said sample collection device during absorption of test liquid;

wherein said assay reagent is present in the downstream part of said absorbing material, said downstream part containing a barrier to prevent said assay reagent from being washed out of the collection device during absorption of said test liquid, said barrier being disposed such that during or after test liquid absorption, said assay reagent is available for test performance, while the upstream part of said absorbing material is entirely or partly located upstream of said downstream part comprising the assay reagent; and wherein said upstream part of said absorbing material is capable of receiving and absorbing test liquid and is disposed between said handle and said downstream part of said absorbing material.

2. A sample collection device according to claim 1, wherein said barrier is a cover, casing or envelop comprising a water repellant material.

3. A sample collection device according to claim 2, wherein said water repellent material is selected from a hydrophobic porous sintered material, a hydrophobic woven on non-woven material, a hydrophobic paper or paper-like material.

4. A sample collection device according to claim 3, wherein said hydrophobic porous sintered material is ethylene vinylacetate, polypropylene or ultra high molecular weight polyethylene, and has a pore size of at most 100 μm.

5. A sample collection device according to claim 1, wherein said barrier is a water impervious material.

6. A sample collection device according to claim 5, wherein said water impervious material is a foil, glass, rubber, a hot melt or solidified pores at the surface of a water repellent material.

7. A sample collection device according to claim 1, wherein said barrier is a reagent composition allowing a controlled release of the assay reagent.

8. A sample collection device according to claim 1, wherein said absorbing material is impregnated with said assay reagent or said assay reagent is entrapped in pores of said absorbing material.

9. A sample collection device according to claim 1, wherein said assay reagent is provided in an interior space in said absorbing material.

10. A sample collection device according to claim 9, wherein said assay reagent is in a freeze-dried form.

11. A sample collection device according to claim 9, wherein said assay reagent is impregnated in a porous carrier.

12. A sample collection device according to claim 1, wherein said absorbing material comprises a porous sintered hydrophilic or hydrophilized material.

13. A sample collection device according to claim 12, wherein said porous sintered hydrophilized material is hydrophilized ethylene vinylacetate, hydrophilized polypropylene, hydrophilized polyethylene or hydrophilized ultra high molecular weight polyethylene.

14. A sample collection device according to claim 13, wherein a pore size of said porous sintered hydrophilized material in the upstream part of said device is larger than that of the porous sintered hydrophilized material in the downstream part of said device.

15. A sample collection device according to claim 1, wherein said assay reagent is a labelled specific binding reagent.

16. A sample collection device according to claim 15, wherein said labelled specific binding reagent comprises a particulate label.

17. A sample collection device according to claim 16, wherein said particulate label is a gold sol or carbon sol.

18. A device for the detection of at least one specifically reacting substance in a test liquid comprising a sample collection device according to claim 1.

19. A device for the detection of at least one specifically reacting substance in a test liquid comprising:

a sample collection device according to claim 1, a housing comprising an interior space and an opening for introducing said sample collection device into said interior space, a holding device located on the housing, a test strip which is held in the holding device and which comprises a material that transports the test liquid essentially by capillary forces and which comprises an immobilized specific binding reagent.

20. A device according to claim 19, wherein the specifically reacting substance is hCG or hLH.

21. A method for the detection of at least one specifically reacting substance in a test liquid, whereby the sample collection according to claim 1 is used.

22. A method according to claim 21, whereby the specifically reacting substance is hCG or hLH.

23. A sample collection device comprising:

an absorbing material capable of absorbing a test liquid and capable of release of said test liquid, said absorbing material having an upstream part and a downstream part and at least one assay reagent;

wherein said assay reagent is present in the downstream part of said absorbing material, said downstream part containing a barrier to prevent said assay reagent from being washed out of the collection device during absorption of said test liquid, said barrier being disposed such that during or after test liquid absorption, said assay reagent is available for test performance, while the upstream part of said absorbing material is entirely or partly located upstream of said downstream part comprising the assay reagent;

said absorbing material further comprising a liquid and reagent releasing part for releasing test liquid and said reagent from said sample collection device;

wherein said upstream part of said absorbing material is capable of receiving and absorbing test liquid, and wherein said downstream part of said absorbing material is disposed between said upstream part and said liquid and reagent releasing part of said absorbing material.

* * * * *